United States Patent [19]

Spivack

[11] Patent Number: 4,474,914
[45] Date of Patent: Oct. 2, 1984

[54] ORTHO-ALKYLATED PHENYL PHOSPHONITES AND STABILIZED ORGANIC COMPOSITIONS

[75] Inventor: John D. Spivack, Spring Valley, N.Y.

[73] Assignee: Ciba-Geigy Corporation, Ardsley, N.Y.

[21] Appl. No.: 499,724

[22] Filed: May 31, 1983

Related U.S. Application Data

[60] Division of Ser. No. 298,032, Aug. 31, 1981, Pat. No. 4,406,842, which is a continuation of Ser. No. 179,848, Aug. 20, 1980, abandoned, which is a continuation of Ser. No. 64,239, Aug. 6, 1979, abandoned, which is a continuation of Ser. No. 898,270, Apr. 20, 1978, abandoned.

[51] Int. Cl.[3] .................................................. C08K 5/53
[52] U.S. Cl. ..................................... 524/100; 524/101; 524/119; 524/126; 524/135
[58] Field of Search ................ 260/962; 524/100, 101, 524/119, 126, 135

[56] References Cited

U.S. PATENT DOCUMENTS

| | | | |
|---|---|---|---|
| 3,055,861 | 9/1962 | Hersh et al. | 524/154 |
| 3,264,324 | 8/1966 | Gould et al. | 260/962 |
| 3,903,208 | 9/1975 | Hofer et al. | 524/135 |
| 3,978,020 | 8/1976 | Liberti | 524/109 |
| 4,143,028 | 3/1979 | Spivack | 524/119 |
| 4,211,731 | 7/1980 | Hofer et al. | 524/126 |
| 4,263,230 | 4/1981 | Uhing | 524/126 |
| 4,341,880 | 7/1982 | Toyoda et al. | 524/101 |

Primary Examiner—Veronica P. Hoke
Attorney, Agent, or Firm—Luther A. R. Hall

[57] ABSTRACT

Ortho-alkylated phenyl phosphonites of the formula

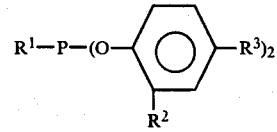

wherein $R^1$ is alkyl, phenyl or phenyl substituted by alkyl, $R^2$ is tertiary alkyl or phenylalkyl, and $R^3$ is hydrogen, alkyl or phenylalkyl are useful as stabilizers for organic polymers and lubricating oils, particularly as processing stabilizers for polyolefins.

10 Claims, No Drawings

ORTHO-ALKYLATED PHENYL PHOSPHONITES AND STABILIZED ORGANIC COMPOSITIONS

This is a divisional of application Ser. No. 298,032, filed on Aug. 31, 1981, now U.S. Pat. No. 4,406,842, issued Sept. 27, 1983, which in turn is a continuation of application Ser. No. 179,848, filed Aug. 20, 1980, now abandoned, which in turn is a continuation of application Ser. No. 064,239, filed Aug. 6, 1979, now abandoned, which in turn is a continuation of application Ser. No. 898,270, filed Apr. 20, 1978, now abandoned.

BACKGROUND OF THE INVENTION

This invention relates to hindered ortho-alkylated phenyl phosphonites which are effective in stabilizing organic materials particularly plastics, polymers and resins as well as mineral and synthetic fluids and oils.

Organic polymeric materials such as plastics, resins, lubricating and mineral and synthetic oils are subject to thermal, oxidative and photodegradation. A great variety of stabilizers are known in the art for stabilizing various substrates. Their effectiveness varies depending on the causes of degradation and the substrate stabilized. It is known that many stabilizers that are very effective long term antioxidants are relatively poor process stabilizers which require stabilization of the substrate, against thermal degradation for a short time, but at a relatively high temperature. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

In Japanese No. 73/41,009 (CA, 81, 121856 g (1974)), a non-hindered phenylphosphonite and a non-hindered phenylthiophosphonite are disclosed as heat stabilizers for ABS, PVC, polyolefins and other polymeric substances.

Diphenylphosphonites, diphenylene bis-phosphonites and terphenylene bis-phosphonites are described in U.S. Pat. No. 3,825,629 as stabilizers for organic materials. These compounds are structurally different from the instant compounds especially in reference to the diphenyl or terphenyl moiety directly attached to the P atom in these molecules.

Thermostabilized linear polyesters containing small amounts of diphenyl phenylphosphonite are claimed in U.S. Pat. No. 3,609,118. This patent contains a very broad generic reference to phenylphosphonites with no subgeneric disclosures and with only diphenyl phenylphosphonite being exemplified.

U.S. Pat. No. 3,809,676 and U.S. Pat. No. 3,978,020 disclose generically some phosphonites of structures related to those of the instant invention, but do not exemplify or specifically mention the hindered phosphonites of this invention. These references respectively pertain to thermally stable flame retardant polycarbonates containing a phosphonite or phosphinite in combination with a barium, calcium or cerium alkanoate or carbonate and to thermally stable polycarbonates containing a phosphonite and an epoxide compound.

The instant phosphonites exhibit surprisingly effective stabilization activity in a variety of substrates and are superior to previously known phosphonites in this stabilization efficacy. The superior performance of the instant phosphonites is particularly evident in those compositions where the effect of water or hydrolysis conditions is minimal.

DETAILED DISCLOSURE

This invention pertains to ortho-alkylated phenyl phosphonites and to organic materials, both polymeric and nonpolymeric, stabilized by said phosphonites.

More particularly, the phosphonites of this invention are represented by the Formula I

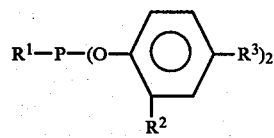

wherein $R^1$ is alkyl of 1 to 18 carbon atoms, phenyl or phenyl substituted by 1 to 3 alkyl groups with 1 to 8 carbon atoms in each alkyl group, $R^2$ is tertiary alkyl of 4 to 18 carbon atoms, benzyl, α-methylbenzyl or α,α-dimethylbenzyl and $R^3$ is hydrogen, alkyl of 1 to 18 carbon atoms, benzyl, α-methylbenzyl or α,α-dimethylbenzyl.

$R^1$ is alkyl of 1 to 18 carbon atoms such as methyl, n-butyl, n-octyl, n-decyl, n-dodecyl or n-octadecyl. $R^1$ can also be phenyl or phenyl substituted by 1 to 3 alkyl groups with 1 to 8 carbon atoms in each alkyl group. Such substituted phenyls would include o-tolyl, m-tolyl, p-tolyl, o-xylyl, m-xylyl, p-xylyl, mesityl, o-cumyl, p-tert-butylphenyl, 2,4,6-tri-tert-butylphenyl or 2,4,-di-tert-octylphenyl.

Preferably $R^1$ is phenyl or phenyl substituted by 1 to 3 alkyl groups with 1 to 4 carbon atoms in each alkyl group.

Most preferably $R^1$ is phenyl.

$R^2$ may be tertiary alkyl of 4 to 18 carbon atoms such as tert-butyl, tert-amyl, tert-octyl or tert-octadecyl. Preferably $R^2$ is tertiary alkyl of 4 to 8 carbon atoms, α-methylbenzyl or α,α-dimethylbenzyl. Most preferably $R^2$ is tertiary alkyl of 4 to 8 carbon atoms, $R^3$ can be alkyl of 1 to 18 carbon atoms such as methyl, isopropyl, tert-butyl, n-hexyl, tert-dodecyl or n-octadecyl. Preferably $R^3$ is hydrogen, alkyl of 1 to 8 carbon atoms, α-methylbenzyl or α,α-dimethylbenzyl. Most preferably $R^3$ is tertiary alkyl of 4 to 8 carbon atoms.

SYNTHESIS OF COMPOUNDS

The compounds of this invention are made by the following procedure:

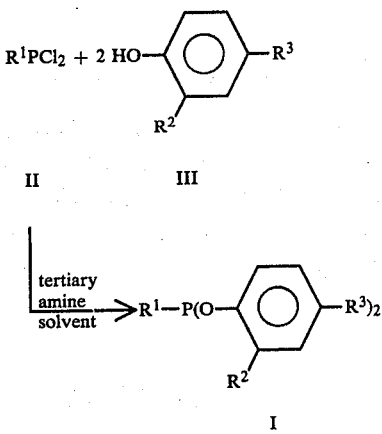

The use of tertiary amines can be avoided by converting the phenols of formula III to the phenolate anion by reaction with stoichiometric amounts of alkali metal or alkali metal hydroxide and subsequently reacting the anion appropriately with II.

Aromatic hydrocarbons such as benzene, toluene or xylene are useful as solvents for the synthesis, but are not essential.

The reaction steps can be conveniently performed by using tertiary amines such as triethylamine, pyridine, N,N-dimethylaniline, but again their use is not essential.

The use of excess tertiary amine over that required as a proton acceptor markedly increases the reaction rates in the synthetic steps. This is particularly important when III is relatively highly hindered phenol.

Reaction temperatures may vary from below room temperature to the reflux temperature of the solvent present. When no solvent is used, temperatures up to about 150° C. are useful.

The various starting materials, i.e., phenols, thiophenols, chlorophosphines, are largely available as items of commerce or can be easily prepared by known methods.

The compounds of this invention are effective light stabilizers and/or antioxidants in a wide range of organic polymers. Polymers which can be stabilized include:

1. Polymers which are derived from mono- or diolefins, e.g., polyethylene which can optionally be cross-linked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene, and copolymers of α-olefins, e.g., ethylene with acrylic or methacrylic acid.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile copolymers modified with acrylic ester polymers to provide impact strength as well as block copolymers, e.g., styrene/butadiene/styrene block copolymers.

6. Graft copolymers of styrene, for example the graft polymer of styrene to polybutadiene, the graft polymer of styrene with acrylonitrile to polybutadiene as well as mixtures thereof with the copolymers cited under (5) commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide or the polymers which are derived from bis-glycidyl ethers.

11. Polyacetals, for example polyoxymethylene, as well as polyoxymethylenes which contain ethylene oxide as comonomer.

12. Polyalkylene oxides, for example polyoxyethylene, polypropylene oxide or polyisobutylene oxide.

13. Polyphenylene oxides.

14. Polyurethanes and polyureas.

15. Polycarbonates.

16. Polysulfones.

17. Polyamides and copolyamides which are derived from diamines and dicarboxylic acids and/or from aminocarboxylic acids or the corresponding lactams, for example polyamide 6, polyamide 6/6, polyamide 6/10, polyamide 11, polyamide 12, poly-m-phenyleneisophthalamide.

18. Polyesters which are derived from dicarboxylic acids and dialcohols and/or from hydroxycarboxylic acids or the corresponding lactones, for example polyethylene glycol terephthalate, poly-1,4-dimethylolcyclohexane terephthalate.

19. Cross-linked polymers which are derived from aldehydes on the one hand and from phenols, ureas and melamine on the other, for example phenol/formaldehyde, urea/formaldehyde and melamine/formaldehyde resins.

20. Alkyd resins, for example glycerol/phthalic acid resins and mixtures thereof with melamine/formaldehyde resins.

21. Unsaturated polyester resins which are derived from copolyesters of saturated and unsaturated dicarboxylic acids with polyhydric alcohols as well as from vinyl compounds as cross-linking agents and also the halogen-containing, flame-resistant modifications thereof.

22. Natural polymers, for example cellulose, rubber, as well as the chemically modified homologous derivatives thereof, for example cellulose acetates, cellulose propionates and cellulose butyrates and the cellulose ethers, for example methyl cellulose.

Compounds of this invention are particularly effective in stabilizing organic materials such as plastics, polymers, resins in addition to mineral and synthetic fluids such as lubricating oils, circulating oils, etc.

The compounds of this invention are particularly useful as stabilizers, especially for the protection of polyolefins, for instance, polyethylene, polypropylene, polyisobutylene, poly(butene-1), poly(pentene-1), poly(3-methylbutene-1), poly(4-methyl-pentene-1), various ethylene-propylene copolymers and the like.

Other substrates in which the compounds of this invention are particularly useful are polystyrene, including impact polystyrene, ABS resin, SBR, polyisoprene, as well as natural rubber, polyesters including polyethylene terephthalate and polybutylene terephthalate, including copolymers. Also stabilized are polyurethanes, polycarbonates, polyamides such as nylon 6, 6/6 and the like as well as copolyamides and polysulfones.

The compounds of this invention may be used alone as the sole stabilizer performing either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

In general, the stabilizers of this invention are employed from about 0.01 to about 5% by weight of the stabilized composition, although this will vary with the particular substrate and application. An advantageous range is from about 0.05 to about 2%, and especially 0.1 to about 1%.

Compounds of this invention stabilize polymers especially during high temperature processing with relatively little change in color, even though the polymer may undergo a number of extrusions. Among the polymers in which this property is especially apparent are polypropylene, polyethylene, styrenics such as ABS, polyethylene- and polybutylene-terephthalates, polycarbonates, natural rubber, synthetic rubber such as SBR. While many compounds which have been used as process stabilizers are only effective as process stabilizers for polyolefins in the presence of phenolic antioxidants, etc., compounds of this invention are effective in the absence of phenolic antioxidants.

Many of the compounds of this invention combine process stabilizing properties with the ability to confer light stability on the polymer. This is particularly important for polymer fibers where processing temperatures are among the highest and where stability to actinic light is a prime requirement.

The stabilizers of Formula I may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain from about 0.01 to about 5%, preferably from about 0.05 to about 2%, and especially from about 0.1% to about 1%, by weight of various conventional additives, such as the following, particularly phenolic antioxidants or UV-absorbers or light-stabilizers, or mixtures thereof:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as for example, 2,5-di-tert.-butyl-hydroquinone, 2,5-di-tert.-amyl-hydroquinone, 2,6-di-tert.-butyl-hydroquinone, 2,5-di-tert.-butyl-4-hydroxy-anisole, 3,5-di-tert.-butyl-4-hydroxy-anisole, tris-(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxypheny) disulfide.

1.4 Alkylidene-bisphenols, such as, for example, 2,2'-methylene-bis-(6-tert.-butyl-4-methylphenol), 2,2'-methylenebis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di(3,-tert.-butyl-5-methyl-2-hydroxybenzyl)-4-methylphenol, 2,2'-methylene-bis-[4-methyl-6-(α-methylcyclohexyl)-phenol], 1,1-bis(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3-tert.-butyl-4-hydroxyphenyl)-butyrate].

1.5 O-, N- and S-benzyl compounds, such as, for example, 3,5,3',5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl) dithioterephthalate.

1.6 Hydroxybenzylated malonates, such as for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7 Hydroxybenzyl-aromatic compounds, such as, for example, 1,3,5-tri-(3,5-di-tert.-butyl-4-hydroxybenzyl)-2,4,6-trimethylbenzene, 1,4-di-(3,5-di-tert-butyl-4-hydroxybenzyl)-2,3,5,6-tetramethylbenzene and 2,4,6-tri(3,5-di-tert.-butyl-4-hydroxybenzyl)-phenol.

1.8 s-Triazine compounds, such as, for example, 2,4-bis-octylmercapto-6-(3,5-di-tert.-butyl-4-hydroxy-anilino)-s-triazine, 2-octylmercapto,4,6-bis-(3,5-di-tert.-butyl-4-hydroxy anilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-s-triazine, 2,4,6-tris-(3,5-di-tert-butyl-4-hydroxyphenylethyl)-s-triazine and 1,3,5-tris-(3,5-di-tert.-butyl-4-hydroxybenzyl)isocyanurate.

1.9 Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di (3,5-di-tert.-butyl-4-hydroxyphenyl-propionyl)-hexamethylenediamine. N,N'-bis-β-(3,5-di-t-butyl-4-hydroxyphenyl)-propionylhydrazine.

1.10 Esters of β-(3,5-di-tert.-butyl-4-hydroxyphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2.2.2]octane.

1.11 Esters of β-(5-tert.-butyl-4-hydroxy-3-methylphenyl)-propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2.2.2]octane.

1.12 Esters of 3,5-di-tert.-butyl-4-hydroxyphenylacetic acid with monohydric or polyhydric alcohols, such as for example, with methanol, ethanol, octadecanol, 1,6-hexandiol, 1,9-nonanediol, ethylene glycol, 1,2-propenediol, diethylene glycol, thio-diethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane, especially the tetrakis ester of pentaerythritol.

1.13 Benzylphosphonates, such as, for example, dimethyl 3,5-di-tert.-butyl-4-hydroxybenzylphosphonate, diethyl 3,5-di-tert.-butyl-4-hydroxybenzylphosphonate, dioctadecyl 3,5-di-tert.-butyl-4-hydroxybenzylphosphonate and dioctadecyl 5-tert.-butyl-4-hydroxy-3-methylbenzylphosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-di-phenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline.

Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamine-acetone condensation product, aldol-1-naphthylamine and phenothiazine.

Discoloration effects have to be taken into account when using the above antioxidants.

2. UV-Absorbers and light-stabilizing agents 2.1 2-(2'-Hydroxyphenol)-benzotriazoles, e.g., the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2 2,4-bis-(2'-Hydroxyphenyl)-6-alkyl-s-triazines, e.g., the 6-ethyl-, 6-heptadecyl- or 6-undecyl-derivative.

2.3 2-Hydroxybenzophenones e.g., the 4-hydroxy-, 4-methoxy-, 4-octoxy, 4-decyloxy-, 4-dodecyloxy-, 4-benzyloxy-, 4,2',4'-trihydroxy- or 2'-hydroxy-4,4'-dimethoxy-derivative.

2.4 1,3-bis-(2'-Hydroxybenzoyl)-benzenes, e.g., 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxybenzoyl)-benzene.

2.5 Esters of optionally substituted benzoic acids, e.g., phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6 Acrylates, e.g., α-cyano-β,β-diphenylacrylic acid-ethyl ester or isoctyl ester, α-carbomethoxy-cinnamic acid methyl ester, α-cyano-β-methyl-p-methoxy-cinnamic acid methyl ester or -butyl ester or N(β-carbomethoxyvinyl)-2-methyl-indoline.

2.7 Sterically hindered amines, e.g., 4-benzoyl-2,2,6,6-tetramethylpiperidine, 4-stearyloxy-2,2,6,6-tetramethylpiperidine, bis-(2,2,6,6-tetramethylpiperidyl)-sebacate or 3-n-octyl-7,7,9,9-tetramethyl-1,3,8-triazaspiro[4.5]decane-2,4-dione.

2.8 Oxalic acid diamides, e.g., 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyloxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g., oxanilide, isophthalic acid dihydrazide, sebacic acid-bis-phenylhydrazide, bis-benzylideneoxalic acid dihydrazide, N,N'-diacetal-adipic acid dihydrazide, N,N'-bis-salicyloyl-oxalic acid dihydrazide, N,N'-bis-salicyloylhydrazine, N,N'-bis-(3,5-di-tert.-butyl-4-hydroxyphenylpropionyl)hydrazine, N-salicyloyl-N'-salicylalhydrazine, 3-salicyloyl-amino1,2,4-triazole or N,N'-bis-salicyloyl-thiopropionic acid dihydrazide.

4. Basic co-stabilizers, e.g., alkali metal salts and alkaline-earth metal salts of higher fatty acids, for example Ca-stearate, Zn-stearate, Mg-behenate, Na-ricinoleate or K-palmitate.

5. Nucleation agents, e.g., 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-isodecyloxy-2,4,8,10-tetraoxa-3,9-diphospha-[5.5]-undecane and tri-(4-hydroxy-3,5-di-tert.butylphenyl) phosphite.

Other additives that can be incorporated in the stabilized compositions are thiosynergists such as dilauryl thiodiproprionate or distearyl thiodipropionate, lubricants such as stearyl alcohol, fillers, carbon black, asbestos, kaolin, talc, glass fibers, pigments, optical brighteners, flameproofing agents and antistatic agents.

The following examples are presented for the purpose of illustration only and are not to be construed to limit the nature or scope of the instant invention in any manner whatsoever.

EXAMPLE 1

O,O'-Bis-(2,4-di-tert-butylphenyl) phenylphosphonite

To a solution of 42.4 grams of 2,4-di-tert-butylphenol in 101 grams of triethylamine was added dropwise over a 15-minute period 17.9 grams of dichlorophenylphosphine. The reaction mixwas then heated for 6 hours at 65°–70° C. After cooling to room temperature, the reaction mixture was diluted with 50 ml of benzene and poured onto a rapidly stirred mixture of 70 grams of concentrated hydrochloric acid and 200 grams of chopped ice. The product was then isolated as in Example 17 with the product crystallized from acetonitrile as white crystals melting at 90°–93° C.

EXAMPLE 2

O,O'-Bis-(2,4-di-tert-octylphenyl) phenylphosphonite

The above-named product was prepared according to the procedure of Example 1 replacing 2,4-di-tert-butylphenol wih an equivalent amount of 2,4-di-tert-octylphenol. The product melted at 80°–83° C.

EXAMPLES 3–8

Other compounds of Formula I may be prepared by the general procedure of Example 1.

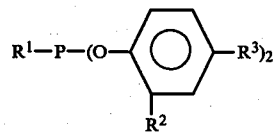

| Example | $R^1$ | $R^2$ | $R^3$ |
|---|---|---|---|
| 3 | phenyl | t-Oc | Me |
| 4 | methyl | t-Oc | t-Oc |
| 5 | n-$C_{12}H_{35}$ | t-Bu | t-Bu |
| 6 | n-$C_{18}H_{37}$ | t-Bu | t-Bu |
| 7 | phenyl | t-Bu | H |
| 8 | phenyl | DMB | DMB | t-BU = tert-butyl
DMB = α,α-dimethylbenzyl
Me = methyl
t-Oc = tert-octyl

EXAMPLE 9

Processing Stability of Polypropylene at 500° F. (260° C.)

The base formulation comprises 100 parts of unstabilized polypropylene (Profax 6801, Hercules) with 0.10 parts of calcium stearate. The test stabilizers were solvent blended into the polypropylene from solutions in methylene chloride. After removal of the solvent by evaporation under reduced pressure, the stabilized resin formulation was extruded at 100 rpm from a 1 inch (2.54 cm) diameter extruder under the following extruder conditions:

| Extruder Location | Temperature | |
|---|---|---|
| | °F. | °C. |
| Cylinder #1 | 450 | 232 |
| Cylinder #2 | 475 | 246 |
| Cylinder #3 | 500 | 260 |
| Die #1 | 500 | 260 |
| Die #2 | 500 | 260 |

During extrusion, the internal extruder pressure was determined using a pressure transducer. After each of the first, third and fifth extrusions, resin pellets were compression molded into 125 mil (3.2 mm) thick plaques at 380° F. (193° C.) and specimen yellowness index (YI) was determined according to ASTM D1925-63T. Low YI values indicate less yellowing.

If the transducer pressure after the fifth extrusion is nearly as high as after the first extrusion, the polypropylene is being well stabilized by the given stabilization formulation.

Results are seen in Tables I–II.

TABLE I

Processing Stability of Polypropylene at 500° F. (260° C.)

| Stabilizer | Conc. Stabilizer % by wt | Transducer Pressure after Extrusion psi/(Kg/cm$^2$) | | | Yellowness Index Color after Extrusion | | |
|---|---|---|---|---|---|---|---|
| | | 1 | 3 | 5 | 1 | 3 | 5 |
| Base formulation | — | 1050/73.5 | 705/49.3 | 525/36.9 | 3.3 | 4.3 | 5.2 |
| IRGANOX 1010* | 0.1 | 1170/82.0 | 975/68.2 | 852/59.6 | 4.5 | 7.6 | 8.8 |
| IRGANOX 1010* (0.1%) plus Compound Ex 1 | 0.05 | 1385/97.0 | 1260/88.1 | 1170/82.0 | 4.4 | 7.2 | 9.5 |

*IRGANOX 1010 = neopentanetetrayl tetrakis(3,5-di-tert-butyl-4-hydroxyhydrocinnamate)

TABLE II

Processing Stability of Polypropylene at 500° F. (260° C.)

| Stabilizer | Conc. Stabilizer % by wt | Transducer Pressure after Extrusion psi/(Kg/cm$^2$) | | | Yellowness Index Color after Extrusion | | |
|---|---|---|---|---|---|---|---|
| | | 1 | 3 | 5 | 1 | 3 | 5 |
| Base formulation | — | 1000/70.0 | 775/54.3 | 625/43.8 | 6.2 | 8.0 | 9.4 |
| IRGANOX 1010* | 0.1 | 1080/75.5 | 930/65.1 | 810/56.7 | 6.7 | 10.2 | 12.8 |
| IRGANOX 1010* | 0.05 | 1320/92.5 | 1165/81.5 | 1050/73.5 | 5.0 | 6.3 | 8.4 |

TABLE II-continued

Processing Stability of Polypropylene at 500° F. (260° C.)

| Stabilizer | Conc. Stabilizer % by wt | Transducer Pressure after Extrusion psi/(Kg/cm$^2$) | | | Yellowness Index Color after Extrusion | | |
|---|---|---|---|---|---|---|---|
| | | 1 | 3 | 5 | 1 | 3 | 5 |
| (0.1%) plus Compound Ex 2 | | | | | | | |

*IRGANOX 1010 = neopentanetetrayl tetrakis(3,5-di-tert-butyl-4-hydroxyhydrocinnamate)

EXAMPLE 10

Processing Stability of High Molecular Weight-High Density Polyethylene at 600° F. (316° C.)

Using the general procedure of Example 9, the processing stability of high molecular weight-high density polyethylene (Union Carbide 10780-64A) having a nominal melt flow rate of 5.0 grams/10 minutes and containing no stabilizer was measured.

The melt flow rate was determined by ASTM method 1238 Condition L. The melt flow rate varies inversely as the transducer pressure and both are relative measures of the molecular weight of the polyethylene. Low melt flow rate indicate higher polymer molecular weights and indicate that polymer degradation by crosslinking may be occurring. Thus, if melt flow rate after the fifth extrusion shows minimum change from that after the first extrusion and if transducer pressure after the fifth is nearly as high as after the first extrusion, the polyethylene is being well stabilized by the given stabilization formulation.

Results are given on Table III.

TABLE III

Processing Stability of High Molecular Weight-High Density Polyethylene at 600° F. (316° C.)

| Stabilizer | Conc. Stabilizer % by wt | Transducer Pressure after Extrusion psi/(Kg/cm$^2$) | | | Melt Flow Rate after Extrusion grams/10 minutes | | | Yellowness Index Color after Extrusion | | |
|---|---|---|---|---|---|---|---|---|---|---|
| | | 1 | 3 | 5 | 1 | 3 | 5 | 1 | 3 | 5 |
| None | — | 1035/72.4 | 1065/74.5 | 1050/73.5 | 3.8 | 3.1 | 2.9 | −0.7 | 1.2 | 1.9 |
| IRGANOX 1076* | 0.1 | 1060/74.1 | 1050/73.5 | 1035/72.4 | 4.4 | 4.1 | 4.0 | −1.2 | 2.5 | 3.5 |
| IRGANOX 1076* (0.1%) plus Compound Ex 2 | 0.5 | 1170/82.0 | 1170/82.0 | 1135/79.4 | 5.0 | 3.8 | 3.4 | −4.1 | −2.2 | −2.0 |
| IRGANOX 1010** | 0.1 | 1065/74.5 | 1050/73.5 | 1020/71.4 | 4.4 | 4.1 | 4.2 | −0.8 | 5.7 | 9.5 |
| IRGANOX 1010** (0.1%) plus Compound Ex 2 | 0.05 | 1155/80.9 | 1140/79.8 | 1105/77.3 | 5.0 | 4.3 | 4.0 | −4.1 | 1.1 | 0.7 |

*IRGANOX 1076 = n-octadecyl 3,5-di-tert-butyl-4-hydroxyhydrocinnamate
**IRGANOX 1010 = neopentanetetrayl tetrakis(3,5-di-tert-butyl-4-hydroxyhydrocinnamate)

EXAMPLE 11

Light Stabilization of Polypropylene

Using an FS/BL radiation unit consisting of 40 tubes of alternating fluorescent sunlamps and black lights (20 of each), 5 mil (0.127 mm) films of polypropylene (Profax 6801, Hercules) containing the test stabilizer and optionally a phenolic antioxidant alone or in combination with a UV absorber were mounted on 3"×2" (7.62 cm×5.08 cm), infrared card holders with 1"×¼" (2.54 cm×0.635 cm) windows and placed on a rotating drum 2 inches (5.08 cm) from the tubes in the FS/BL unit. The time in hours required for development of 0.5 carbonyl absorbance units in the test films as determined by infrared spectroscopy was noted. The development of carbonyl groups in the polypropylene is proportional to the amount of degradation caused by the ultraviolet light exposure.

The test results are given on Table IV.

TABLE IV

| Stabilizer (% by weight) | Hours to Failure (Development 0.5 carbonyl absorbance unit) |
|---|---|
| None | 200 |
| Compound Example 1 (0.3%) | 570 |
| Compound Example 1 (0.5%) plus IRGANOX 1093* (0.2%) | 680 |
| Compound Example 1 (0.25%) plus IRGANOX 1093 (0.2%) plus TINUVIN 327** (0.25%) | 1350 |
| Compound Example 2 (0.5%) plus IRGANOX 1093 (0.2%) | 530 |
| Compound Example 2 (0.25%) plus IRGANOX 1093 (0.2%) plus TINUVIN 327 (0.25%) | 1350 |

*IRGANOX 1093 = di-n-octadecyl 3,5-di-tert-butyl-4-hydroxybenzylphosphonate.
**TINUVIN 327 = 5-chloro-2-(2-hydroxy-3,5-di-tert-butylphenyl)-2H-benzotriazole.

EXAMPLE 12

Stabilization of Polyethylene Terephthalate

1% of the compound of Example 1 is added as a stabilizer to molten polyethylene terephthalate at 270° C. with stirring under a nitrogen atmosphere. The resulting formulated polymer is ground with solid carbon dioxide until the particle size is less than 100 microns in diameter. The temperature at which the onset of oxidation takes place is then determined as follows:

About 1 milligram of the polyester powder, as prepared above, is charged into the chamber of the Perkin-Elmer Differential Scanning Calorimeter and heated under nitrogen till a temperature of 225° C. is reached. The nitrogen flow is stopped and oxygen is introduced at a rate of 15 ml per minute while heating at a rate of 1 degree per minute until the oxidation exotherm is recorded. The oxidation temperature of the formulated powder is thus determined to be higher than that of the base polyester powder without the stabilizer. The higher oxidation temperature provided by the stabilizer clearly shows the marked improvement in inhibition of oxidation of the polyester. The color of the stabilized polyester is also improved compared to that without the additive.

EXAMPLE 13

Stabilization of Acrylonitrile-Butadiene-Styrene (ABS)

ABS resin is prepared by heating at 80° C. for 7.5 hours the following formulations:

| Resin A: | butadiene | 10 parts |
| --- | --- | --- |
| | acrylonitrile | 24 |
| | styrene | 65.8 |
| | 2,2'-azobisisobutyronitrile | 0.1 |
| | | 99.9 parts |

Resin B: This resin is prepared in the same manner as Resin A except that it contains additionally 0.25% of the stabilizer.

The oxidation temperature of each of the resins is determined by Differential Scanning Calorimetry (DSC) employing the following procedure:

10 mg is charged to the DSC pan and heated from ambient temperature at a rate of 20° C./minute in an oxygen stream flowing at the rate of 250 ml/minute. The temperature at which an exotherm is observed for each of the resins is recorded.

Samples of ABS resins each made with 0.25% of a stabilizer of Examples 1 and 2 both exhibit an exotherm at a higher temperature than does the corresponding ABS resins containing no stabilizer indicating higher thermal stability for the stabilized resins.

EXAMPLE 14

Stabilization of Polycarbonate

Polycarbonate (Lexan, General Electric) is formulated by mixing the base resin in a Waring Blender with 0.1% the compound of Example 1, the base resin also containing 0.1% of octadecyl 3,5-di-t-butyl-4-hydroxyhydrocinnamate. The formulated resin is compression molded, cut into chips and charged into a standard melt index apparatus. After maintaining at 350° C. for 30 minutes a sample is removed compressed into plaques and examined for color. The sample containing both stabilizers is much lighter in color than that containing only octadecyl 3,5-di-t-butyl-4-hydroxyhydrocinnamate.

What is claimed is:

1. A composition of matter comprising an organic material subject to oxidative, thermal or actinic degradation stabilized with from 0.01 to 5% weight of a compound of the formula

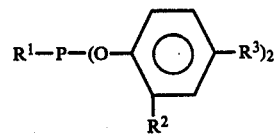

wherein
R$^1$ is alkyl of 1 to 18 carbon atoms, phenyl or phenyl substituted by 1 to 3 alkyl groups with 1 to 8 carbon atoms in each alkyl group,
R$^2$ is tertiary alkyl of 4 to 18 carbon atoms, benzyl, α-methylbenzyl or α,α-dimethylbenzyl, and
R$^3$ is hydrogen, alkyl of 1 to 18 carbon atoms, benzyl, α-methylbenzyl or α,α-dimethylbenzyl.

2. A composition according to claim 1 wherein the organic material is a synthetic polymer.

3. A composition according to claim 2 wherein the polymer is a polyolefin homopolymer or copolymer.

4. A composition according to claim 3 stabilized with O,O'-bis(2,4-di-tert-butylphenyl) phenylphosphonite or O,O'-bis (2,4-di-tert-octylphenyl) phenylphosphonite.

5. A composition according to claim 2 which additionally contains from 0.01 to 5% by weight of a phenolic antioxidant.

6. A composition according to claim 5 wherein the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate and 1,3,5-tris(3,5-di-tert-butyl-4-hydroxybenzyl)isocyanurate.

7. A composition according to claim 2 which additionally contains from 0.01 to 5% by weight of phenolic antioxidant and from 0.01 to 5% by weight of a UV absorber or light stabilizer.

8. A composition according to claim 7 wherein the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydroxcnnamate), di-n-octadecyl 3,5-di-tert-butyl-4-hydroxybenzylphosphonate and 1,3,5-tris(3,5-di-tert-butyl-4-hydroxybenzyl)isocyanurate and the UV absorber is selected from the group consisting of 5-chloro-2-(2-hydroxy-3,5-di-tert-butylphenyl)-2H-benzotriazole and 2-(2-hydroxy-3,5-di-tert-amylphenyl)-2H-benzotriazole.

9. A composition according to claim 2 which additionally contains from 0.01 to 5% by weight of a UV absorber or light stabilizer.

10. A composition according to claim 9 wherein the UV absorber is selected from the group consisting of 5-chloro-2-(2-hydroxy-3,5-di-tert-butylphenyl)-2H-benzotriazole and 2-(2-hydroxy-3,5-di-tert-amylphenyl)-2H-benzotriazole.

* * * * *